(12) United States Patent
Kirchhoff et al.

(10) Patent No.: US 12,350,387 B2
(45) Date of Patent: Jul. 8, 2025

(54) METHOD FOR INACTIVATING BIOLOGICALLY ACTIVE COMPONENTS IN A LIQUID

(71) Applicant: Fraunhofer-Gesellschaft zur Förderung der angewandten Forschung e.V., Munich (DE)

(72) Inventors: Volker Kirchhoff, Dresden (DE); André Weidauer, Dresden (DE); Jessy Schönfelder, Dresden (DE); Gaby Gotzmann, Dresden (DE); Christiane Wetzel, Dresden (DE); Jörg Kubusch, Dresden (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 796 days.

(21) Appl. No.: 17/282,516

(22) PCT Filed: Sep. 25, 2019

(86) PCT No.: PCT/EP2019/075926
§ 371 (c)(1),
(2) Date: Apr. 2, 2021

(87) PCT Pub. No.: WO2020/069942
PCT Pub. Date: Apr. 9, 2020

(65) Prior Publication Data
US 2021/0379218 A1    Dec. 9, 2021

(30) Foreign Application Priority Data
Oct. 5, 2018 (DE) ..................... 10 2018 124 664.1

(51) Int. Cl.
*A61L 2/08* (2006.01)
*A61L 2/26* (2006.01)
*A61L 11/00* (2006.01)

(52) U.S. Cl.
CPC ................. *A61L 2/087* (2013.01); *A61L 2/26* (2013.01); *A61L 11/00* (2013.01);
(Continued)

(58) Field of Classification Search
CPC . A61L 2/087; A61L 2/26; A61L 11/00; A61L 2202/11; A61L 2202/122; A61L 2202/14; A01K 41/10
See application file for complete search history.

(56) References Cited

U.S. PATENT DOCUMENTS 4,201,918 A * 5/1980 Latzer .................... B01J 19/085
250/492.1
2003/0174810 A1    9/2003 Korenev et al.
(Continued)

FOREIGN PATENT DOCUMENTS

CN    105431171 A    3/2016
DE    199 42 142 A1    3/2001
(Continued)

OTHER PUBLICATIONS

Machine Translation of "Kretzschmar", EP 1702678 A1, filed Sep. 22, 2022 (Year: 2006).*
(Continued)

*Primary Examiner* — Jennifer Wecker
*Assistant Examiner* — Brady C Pilsbury
(74) *Attorney, Agent, or Firm* — Crowell & Moring LLP

(57) ABSTRACT

A method may be provided for inactivating biologically active components in a liquid using low-energy electrons generated by an electron source, the electrons having an acceleration voltage of 25 keV to 300 keV. The method
(Continued)

comprises the following steps: a) filling a vessel with a liquid volume; b) applying low-energy electrons to a first partial volume of the liquid filled into the vessel, wherein the first partial volume is a maximum of 10% of the liquid volume in the vessel; c) mixing the first partial volume of the liquid, applied with the low-energy electrons, to the second partial liquid volume in the vessel, which has not been applied with low-energy electrons; d) repeating steps b) and c) several times.

11 Claims, 2 Drawing Sheets

(52) U.S. Cl.
CPC ...... *A61L 2202/11* (2013.01); *A61L 2202/122* (2013.01); *A61L 2202/14* (2013.01)

(56) References Cited

U.S. PATENT DOCUMENTS

| | | | |
|---|---|---|---|
| 2003/0190272 A1 | 10/2003 | Raine et al. | |
| 2004/0219056 A1* | 11/2004 | Tribelsky | B65B 55/08 422/22 |
| 2015/0044093 A1* | 2/2015 | Goodwin | A61L 2/26 250/428 |
| 2016/0158339 A1* | 6/2016 | Ulbert | A61K 41/10 424/206.1 |
| 2016/0158394 A1 | 6/2016 | Goodwin et al. | |
| 2017/0239637 A1* | 8/2017 | Bourke, Jr. | B01J 19/128 |
| 2019/0175769 A1* | 6/2019 | Schönfelder | A61L 2/007 |

FOREIGN PATENT DOCUMENTS

| | | | |
|---|---|---|---|
| DE | 10 2016 216 573 A1 | 3/2018 | |
| EP | 0 024 487 A1 | 11/1981 | |
| EP | 1 702 678 A1 | 9/2006 | |
| EP | 2135624 A1 | 12/2009 | |
| WO | WO 90/11095 A2 | 10/1990 | |
| WO | WO 01/23007 A1 | 4/2001 | |
| WO | WO-02083295 A1 * | 10/2002 | ............ A61L 2/087 |
| WO | WO 2004/101003 A1 | 11/2004 | |
| WO | WO 2015/058971 A1 | 4/2015 | |

OTHER PUBLICATIONS

B. Bogdanovitch et al., "Application of Low Energy Electron Beams for Technology and Medicine", Proceedings of the 1999 Particle Accelerator Conference, New York (Year: 1999).*
International Search Report for Patent Application No. PCT/EP2019/075926, dated Mar. 10, 2020, pp. 1-4.
Office Action dated Dec. 7, 2022 for China Patent Application No. 201980065229.4 (English and Chinese languages) (15 pp.).
Radiation Applications, Institute of Scientific and Technical Information of China, Chongging Branch, Jun. 30, 1981 (3 pp.).
German Office Action with English translation for German Patent Application No. DE 10 2018 124 664.1, dated May 3, 2020, pp. 1-7.
Article in German with English translation, titled, "Award for innovative developments in the use of low-energy electrons for medical applications", Dresden, Germany, dated Dec. 20, 2017, obtained from the Internet at: https://www.fep.fraunhofer.de/de/de/press_media/Pressemitteilungen2017/26_2017.html, pp. 1-4.
Office Action dated Jul. 15, 2022 for China Patent Application No. 201980065229.4 (Chinese language only( (8 pp.).
Office Action dated Aug. 6, 2024 for Korean Patent Application No. 10-2021-7013577 (Korean language and English translation) (24 pp.).

* cited by examiner

METHOD FOR INACTIVATING BIOLOGICALLY ACTIVE COMPONENTS IN A LIQUID

CROSS-REFERENCE TO RELATED APPLICATIONS

This application is a 371 nationalization of international patent application PCT/EP2019/075926 filed Sep. 25, 2019, which claims priority under 35 USC § 119 to German patent application 102018124664.1 filed Oct. 5, 2018. The entire contents of each of the above-identified applications are hereby incorporated by reference.

DETAILED DESCRIPTION

Figure 1:
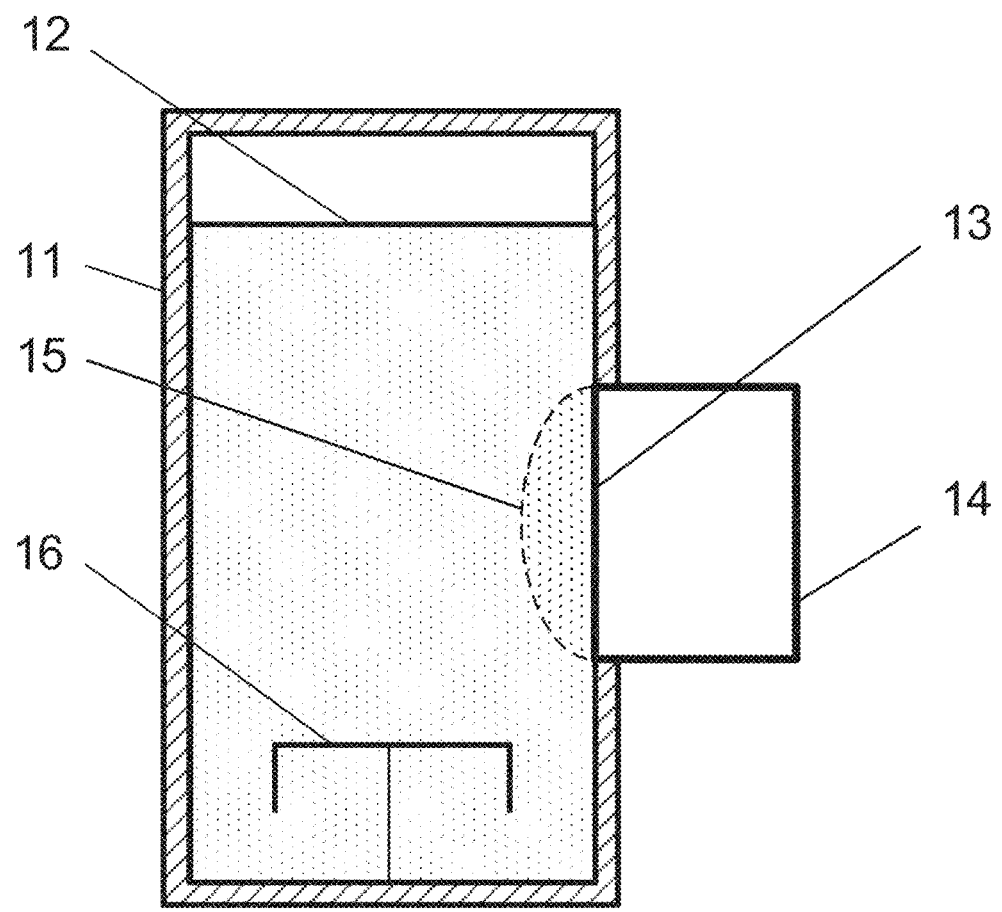
FIG. 1 a schematic sectional view of an apparatus suitable for carrying out the method according to the invention.

The invention relates to a method for inactivating biologically active components in a liquid.

Liquid wastes which contain biologically active components such as microorganisms or plant remains arise chiefly in the pharmaceutical and biotechnology industries, as a consequence of animal experiments, in the disposal of animal bodies, in waste and wastewater treatment and in livestock farming in the form of slurry, to name just a few examples.

Biologically-contaminated liquid or solid wastes are assigned to various biosafety classes. Previously, such wastes were predominantly inactivated by chemical or thermal means, i.e., the microbiological contamination in the form of viruses, bacteria, microfungi and possibly prions was eliminated.

In the following, the term "inactivate" should be understood to mean that the health-damaging effect of biologically active components of a liquid is eliminated. On one hand, this can mean that the biologically active components of a liquid are sterilized and/or destroyed. But on the other hand, it may suffice if the biologically active components of the liquid are affected in such a way that they are no longer capable of reproducing or that the number of biologically active components of the liquid which are capable of reproducing is reduced in order to inhibit the health-damaging effect thereof. The designation "biologically active components" thus includes all such components which trigger a reaction in living organisms. Accordingly, biologically active components of a liquid can be, for example, viruses, bacteria, fungi, yeasts, algae, prions, protozoa, plant components or hormones. This list is intended merely as an example and is not to be considered as complete.

The type of microbiologically contaminated waste ranges from aqueous liquids and chicken eggs from vaccine production to animal bodies such as lab mice, for example. However, slurry originating from livestock farming is often contaminated with bacteria such as *Salmonella*, which should be inactivated before the slurry is spread on fields.

Depending on the type of waste and contamination (hazardous nature of the viruses, bacteria, microfungi or prions), known methods of inactivation are associated with risks and in some cases considerable disadvantages. For example, thermal methods, in particular, require a considerable energy expenditure because temperatures greater than 70° C. or even above 130° C. and long exposure times are required.

A further method is inactivation by burning. However, in this case the product is destroyed and no further use is possible.

Chemical methods such as the inactivation of wastes from vaccine production (for example incubated chicken eggs) are often based on a treatment with acids or bases. This is associated with the risk of not every volume element being taken into account when larger volumes are inactivated. Furthermore, this method entails considerable holding times in order to ensure the necessary minimum contact time of the acids or bases.

The fact that germs or microorganisms can be killed by means of accelerated electrons is known. In DE 199 42 142 A1, for example, seed during multiple passes in free fall is bombarded with accelerated electrons in order to kill germs on the seed. The inherent disadvantage of this method lies in that it is not suitable for germ reduction in masses which have liquid components.

Proposals in which liquids are bombarded with accelerated electrons for killing germs are known from the field of water purification. For example, EP 0 024 487 A1 shows a solution in which a liquid is first conveyed onto a platform, from which it falls down as a liquid curtain. As it falls, it is irradiated once from one side. The disadvantage herein lies in that components of the liquid at the front side of the liquid curtain are bombarded with a higher radiation dose than components at the back side of the liquid curtain. If the aim is also to inactivate all biologically active components at the back side of the liquid curtain with the single irradiation process, then the setting of the radiation must be so strong that it may result in the damaging or destruction of the biologically active components at the front side of the liquid curtain.

However, in some applications such as, for example, the inactivation of biologically active components in bioreactors for vaccine production, it may be necessary to inactivate biologically active components of a liquid without the biologically active components being damaged or destroyed, as the latter are subsequently needed for obtaining the vaccine.

A method for inactivating pathogens in biological media is known from DE 10 2016 216 573 A1, in which the bottom of a roller set in rotation is partially immersed in a liquid such that, as a consequence of the turning of the roller, a liquid film forms on the top of the roller and is bombarded with ionizing radiation. After the bombardment of the liquid film with ionizing radiation, the liquid film is scraped off of the roller and fed into subsequent processes. Because the liquid of the liquid film is likewise only bombarded once and only from one side with this known method, the disadvantages described above are also associated with this solution.

The invention is therefore based on the technical problem of creating a method for inactivating a liquid containing biologically active components, by means of which the disadvantages of the prior art can be overcome. In particular, with the method according to the invention it should also be possible to inactivate biologically active components of a liquid without destroying or damaging the biologically active components of the liquid.

Whereas in methods of the prior art an attempt is often made to treat a batch of material with accelerated electrons completely in a single irradiation pass, wherein high-energy, accelerated electrons are usually employed, the method according to the invention is based on bombarding only partial volumes of a batch of material with accelerated electrons, but on doing so several times and with very low doses of accelerated electrons.

In the method according to the invention, biologically active components in a liquid are inactivated by means of low-energy electrons generated by an electron source. In the sense of the invention, low-energy electrons are electrons with an acceleration voltage of 25 keV to 300 keV. First, a vessel is filled with a liquid volume of the liquid containing biologically active components. Such a vessel can be, for example, a bioreactor or any other vessel which is suitable for holding a liquid. Next, a first partial volume of the liquid added to the vessel is bombarded with low-energy electrons, wherein the first partial volume comprises a maximum of 10% of the liquid volume in the vessel. The method according to the invention is further characterized in that at least 90% of the energy of the low-energy electrons generated by the electron source is applied within the first partial volume. The partial volume in the vessel at a given time that was not bombarded with accelerated electrons at this time or into which a maximum of 10% of the energy of the low-energy electrons is input is designated as the second partial volume. After the bombardment of the first partial volume, the first partial volume of the liquid which was bombarded with low-energy electrons is mixed with the second liquid partial volume in the vessel which was not bombarded with low-energy electrons. Subsequently, a first partial volume of the liquid added to the vessel is bombarded with low-energy electrons again and then mixed with the second partial volume that was not bombarded with low-energy electrons. The bombardment of a first volume with low-energy electrons and the mixing of the first partial volume with the second partial volume is repeated several times and until all biologically active components of the liquid volume in the vessel have been inactivated.

Due to the fact that the partial volume is relatively small in relation to the entire volume in a vessel and that the small partial volume is only bombarded with low-energy electrons, it is possible to implement a gentle inactivation of biologically active components in a liquid without damaging or destroying the biologically active components in the liquid. Therefore, it is particularly advantageous if the first partial volume bombarded with low-energy electrons only comprises a maximum of 5% of the liquid volume in the vessel.

Also advantageous for a gentle inactivation of biologically active components in a liquid is if the first partial volume of the liquid is bombarded during an irradiation time interval with a maximum of 1% of the total of low-energy electrons required for inactivating all biologically active components in the first partial volume of the liquid. The application of such a low dose of low-energy electrons to a relatively small partial volume to be irradiated requires repeated irradiation of first partial volumes and repeated mixing of a currently irradiated partial volume with a currently non-irradiated second partial volume in each case in order to inactivate all biologically active components in the entire liquid volume in the vessel. However, this is advantageous in that all particles of the liquid are irradiated with the same total dose of low-energy electrons on average.

In an embodiment of the method according to the invention, a subarea of a wall of the vessel is designed as an electron exit window of the electron source, through which low-energy electrons enter the first partial volume of the liquid in the vessel, wherein means for mixing the liquid in the vessel cause the composition of the first partial volume of the liquid in the vessel to change.

However, as an alternative the first partial volume of the liquid volume can also be extracted from the vessel, bombarded with low-energy electrons outside the vessel, and afterwards mixed with the second liquid volume remaining in the vessel.

In the following, this invention will be explained in more detail, with reference to exemplary embodiments.

FIG. 1 shows a schematic cutaway view of an apparatus which is suitable for carrying out the method according to the invention. First, a vessel 11 is filled with a liquid volume 12 of a liquid containing biologically active components and in which the biologically active components are to be inactivated. A wall of the vessel 11 is designed, in a region, as an electron exit window 13 of an electron source 14. Through the electron exit window 13, low-energy electrons with an acceleration voltage of 25 keV to 300 keV enter a first partial volume 15 of the liquid volume 12. It is known that the penetration depth of accelerated electrons and the distribution of the energy input into the medium as a result can also be calculated in a medium such as a liquid such that a person skilled in the art can adjust the electrical parameters of the electron source 14 according to the invention in such a way that the first partial volume 15 bombarded with the low-energy electrons of the electron source 14 makes up a maximum of 10% and preferably a maximum of 5% of the liquid volume 12 and that at least 90% of the energy of the low-energy electrons is input into this first partial volume 15.

During an irradiation time interval, the first partial volume 15 of the liquid is preferably bombarded with a maximum of 1% of the total of low-energy electrons required to inactivate all biologically active components in the first partial volume 15 of the liquid. In laboratory experiments, it is possible to determine the dose of low-energy electrons required to inactivate all biologically active components of a partial volume 15. On the basis thereof, a person skilled in the art can also adjust the electrical parameters of the electron source 14 in such a way that during an irradiation time interval, a maximum of 1% of the total of low-energy electrons required to inactivate all biologically active components in the partial volume 15 enters the partial volume 15.

Means 16 ensure that a first partial volume 15 bombarded with low-energy electrons is mixed with the second partial volume not bombarded with low-energy electrons, whereby the composition of the first partial volume 15 also changes and a new first partial volume 15 is continuously formed.

The bombardment of first partial volumes 15 with low-energy electrons and the mixing of the liquid in the vessel 11 are continued until a liquid sample extracted from the vessel 11 indicates that the biologically active components in the liquid have been sufficiently inactivated.

In one embodiment, the electron source 14 is operated continuously and with constant output during the entire process of inactivating all biologically active components in the liquid volume 12. Alternatively, the electron source 14 can also be activated only periodically in time intervals, wherein the time segments of the activation of the electron source can be the same length or different lengths.

In a further embodiment, the liquid in the vessel 11 is mixed continuously with the means 16 during the entire process of inactivating all biologically active components in a liquid volume 12 in the vessel 11. Alternatively, the liquid in the vessel 11 can also be mixed only periodically in time intervals, wherein the time intervals can be the same length or different lengths.

Figure 2:
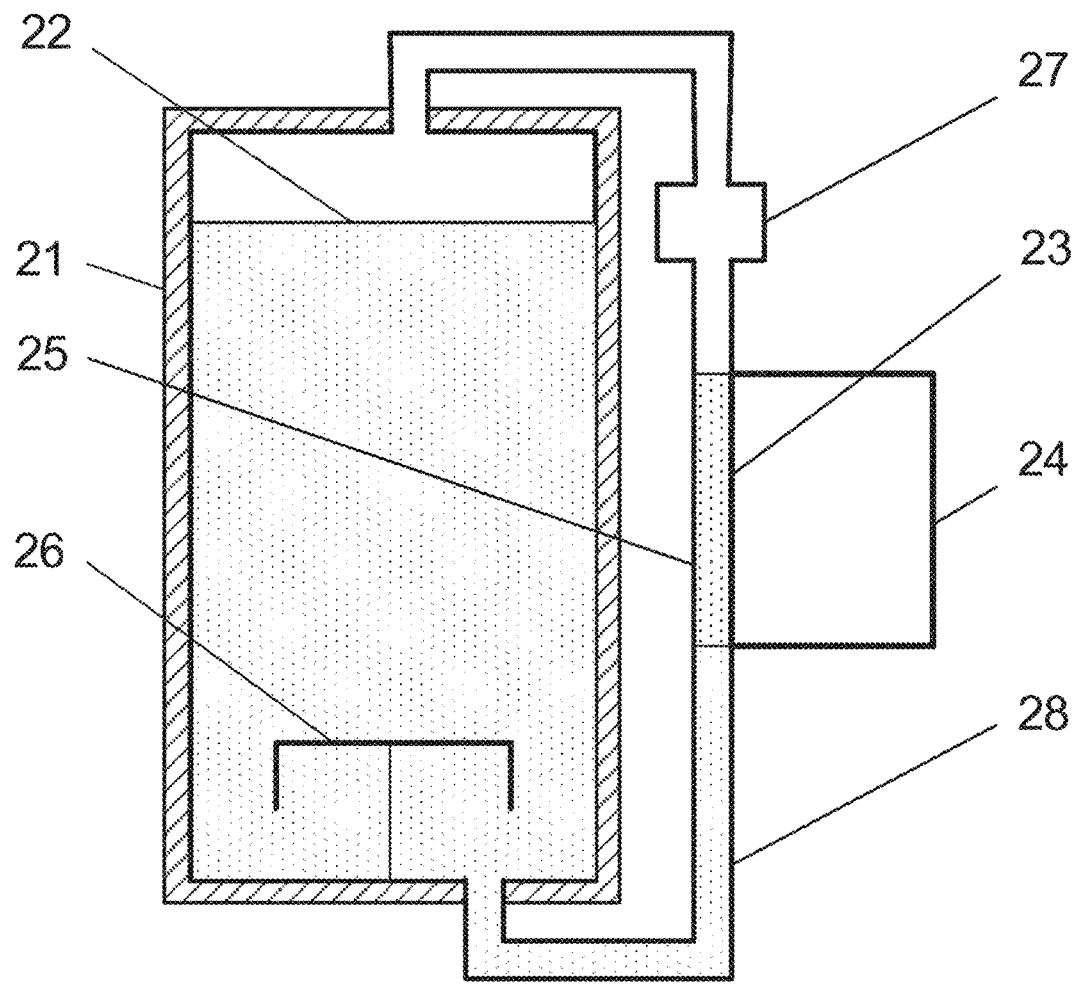
FIG. 2 a schematic sectional view of an alternative apparatus suitable for carrying out the method according to the invention.

An alternative apparatus for carrying out the method according to the invention is schematically shown in a cutaway view in FIG. 2. A vessel 21 is first filled with a liquid volume 22 of a liquid containing biologically active components, in which the biologically active components are to be inactivated. By means of at least one pump device 27, a continuous flow of the liquid in the vessel 21 is branched off, conveyed through a pipeline 28 and then fed back to the vessel 21.

A wall of the pipeline 28 is designed in a region as an electron exit window 23 of an electron source 24. Through the electron exit window 23, low-energy electrons with an acceleration voltage of 25 keV to 300 keV enter a first partial volume 25 of the liquid volume 22. The pipeline 28 and the electron source 24 are dimensioned in such a way that the low-energy electrons generated by the electron source 24 only bombard a first partial volume 25 in each case, which makes up a maximum of 10% and preferably a maximum of 5% of the liquid volume 22, wherein at least 90% of the energy of the low-energy electrons is input into the first partial volume 25.

In this procedure, the flow velocity of the liquid in the pipeline 28 and the electrical parameters of the electron source 24 are adjusted in such a way that a maximum of 1% of the total of low-energy electrons required to inactivate all biologically active components in the first partial volume 25 penetrate into a first partial volume 25 in one pass (in other words, when the first partial volume flows past the electron exit window 25 [sic] one time).

The bombardment of first partial volumes 25 with low-energy electrons and the mixing of the liquid in the vessel 21 are continued until a liquid sample extracted from the vessel 21 indicates that the biologically active components in the liquid have been sufficiently inactivated.

If the continuous flow of the liquid in the vessel 21 is branched off in a lower region of the vessel 21 and reintroduced in an upper region of the vessel 21, as illustrated in FIG. 2, then this process alone ensures a constant mixing of the liquid in the vessel 21. Additionally, the liquid in the vessel 21 can also be mixed, either continuously or in time intervals, with the aid of means 26.

In proportion to the methods known from the prior art, the procedures according to the invention described with reference to FIGS. 1 and 2 require a relatively long time to inactivate biologically active components in a liquid, but they are advantageous in application cases in which all components of a liquid are bombarded with an entirely homogenous dose of accelerated electrons and/or in which the biologically active components are not to be destroyed. The method according to the invention can be used in, for example, bioreactors for the production of vaccines, or also in wastewater treatment.

In the exemplary embodiments described with reference to FIGS. 1 and 2, at least one sensor can be arranged in the regions of the first partial volumes 15 or 25, with which the intensity of the flow of accelerated, low-energy electrons, the distribution thereof in the partial volume 15 or 25 and/or the dose of the low-energy electrons applied in the partial volume 15 or 25 can be recorded and controlled by means of an analysis device.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. A method for inactivating biologically active components in a liquid, the method comprising:
    pouring a liquid into a vessel forming a liquid volume;
    irradiating a first partial volume of the liquid volume with a plurality of low-energy electrons, wherein the low-energy electrons are generated by an electron source and have an acceleration voltage of 25 keV to 300 keV, further wherein the first partial volume comprises a maximum of 10% of the liquid volume in the vessel;
    mixing the first partial volume of the liquid irradiated with the low-energy electrons with a second partial volume of the liquid in the vessel that was not irradiated with the low-energy electrons; and
    repeating the irradiating of the first partial volume and the mixing of the first partial volume with the second partial volume a plurality of times for inactivating the biologically active components in the liquid;
    wherein a sub-area of a wall of the vessel is designed as an electron exit window of the electron source, through which low-energy electrons penetrate into the first partial volume of the liquid in the vessel and where the electron exit window has a direct contact with the first partial volume of the liquid, wherein means for mixing the liquid in the vessel cause the composition of the first partial volume of the liquid in the vessel to change.

2. The method of claim 1, wherein the first partial volume of the liquid is irradiated with a maximum of 1% of the total of low-energy electrons required to inactivate all biologically active components in the first partial volume of the liquid.

3. The method of claim 1, wherein the electron source is operated continuously during the entire process of inactivating all biological active components in the liquid.

4. The method of claim 1, wherein the electron source is activated periodically.

5. The method of claim 1, wherein the liquid in the vessel is mixed continuously during the entire process of inactivating all biologically active components in the liquid volume in the vessel.

6. The method of claim 1, wherein the liquid in the vessel is mixed periodically.

7. The method of claim 1, wherein the liquid in the vessel is mixed continuously.

8. The method of claim 1, wherein the first partial volume comprises a maximum of 5% of the liquid volume in the vessel.

9. The method of claim 1, wherein the first partial volume is irradiated with at least 90% of the energy of the low-energy electrons generated by the electron source.

10. The method of claim 1, further comprising repeating the irradiating of the first partial volume and the mixing of the first partial volume with the second partial volume until biologically active components of a liquid in the vessel are inactivated.

11. The method of claim 1, wherein the vessel is a bioreactor.

* * * * *